United States Patent [19]

Saulnier et al.

[11] Patent Number: 4,888,419
[45] Date of Patent: Dec. 19, 1989

[54] 3'-DEMETHOXYEPIPODOPHYLLOTOXIN GLUCOSIDE DERIVATIVES

[75] Inventors: Mark G. Saulnier, Middletown; Dolatrai M. Vyas, Madison, both of Conn.

[73] Assignee: Bristol-Myers Company, New York, N.Y.

[21] Appl. No.: 91,570

[22] Filed: Aug. 31, 1987

[51] Int. Cl.[4] .................. C07H 15/26; A61K 31/70
[52] U.S. Cl. .................... 536/18.1; 536/18.2; 536/18.7; 536/54; 536/4.1; 514/33; 514/35; 514/27; 514/908
[58] Field of Search .............. 536/18.1, 18.2, 4.1, 536/54; 514/33, 35, 908, 27

[56] References Cited

U.S. PATENT DOCUMENTS

| 608,815 | 11/1960 | Kussmaul et al. | 536/18.1 |
|---|---|---|---|
| 3,408,441 | 10/1968 | Wartburg et al. | 536/18.1 |
| 3,524,844 | 8/1970 | Keller-Juslen et al. | 536/18.1 |
| 4,547,564 | 10/1985 | Umezawa et al. | 536/18.1 |
| 4,609,644 | 9/1986 | Nemec | 536/18.1 |
| 4,757,138 | 7/1988 | Fujii et al. | 536/4.1 |

FOREIGN PATENT DOCUMENTS

| 0141057 | 5/1985 | European Pat. Off. | 536/18.1 |
|---|---|---|---|
| 0823068 | 11/1959 | United Kingdom | 536/18.1 |
| 1162248 | 8/1969 | United Kingdom | 536/18.1 |
| 86/00018 | 1/1986 | World Int. Prop. O. | 536/18.1 |

OTHER PUBLICATIONS

Electroanal. Chem. (184(2):317–29); Holthuis et al. (1985).

Primary Examiner—Ronald W. Griffin
Assistant Examiner—Nancy S. Carson
Attorney, Agent, or Firm—Mollie M. Yang

[57] ABSTRACT

This invention relates to novel 3'-demethoxy epipodophyllotoxin glucosides, their use as anti-tumor agents, and pharmaceutical compositions thereof.

4 Claims, No Drawings

3′-DEMETHOXYEPIPODOPHYLLOTOXIN GLUCOSIDE DERIVATIVES

BACKGROUND OF THE INVENTION

1. Field of the Invention

The present invention relates to 3′-demethoxy epipodophyllotoxin glucoside derivatives, to their therapeutic anti-tumor use, and to pharmaceutical dosage forms containing these new agents.

2. Description of the Related Art

Etoposide (VP-16, Ia) and teniposide (VM-26, Ib) are clinically useful anticancer agents derived from the naturally occurring lignan, podophyllotoxin (II). The numbering system used for nomenclature purposes is shown in Formula II. Etoposide and teniposide are 4′-demethyl epipodophyllotoxin derivatives; epipodophyllotoxin being

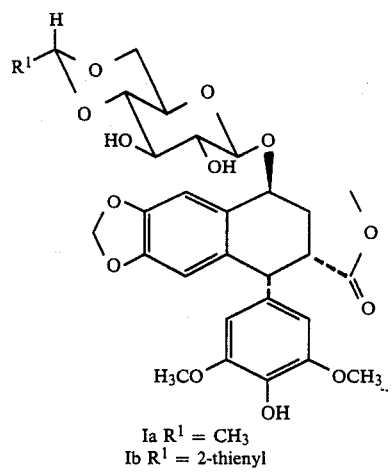

Ia $R^1$ = $CH_3$
Ib $R^1$ = 2-thienyl

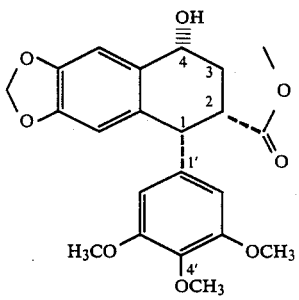

the epimer of podophyllotoxin at the 4-position. Etoposide and teniposide are active in the treatment of a variety of cancers including small cell lung cancer, non-lymphocytic leukemia, and non-seminomatous testicular cancer (AMA Drug Evaluation, 5th Edition, American Medical Association, 1983, Chicago, Ill., p. 1554–5).

Etoposide and teniposide, and methods for producing them, are disclosed in U.S. Pat. No. 3,524,844 to Keller-Juslen et al. Etoposide 3′, 4′-quinone (IIIa) has been generated from electrochemical oxidation of etoposide (Holthuis J. J. M., et al, J. Electroanal. Chem. Interfacial Electrochem., 1985, 184(2):317-29). The preparation of the quinone III by chemical oxidation is disclosed in US patent 4,609,644 to Josef Nemec. Epipodophyllotoxin 3′, 4′-quinone derivatives III wherein $R^1$ and $R^2$ have the definition given hereinbelow for Formula IV serve as the starting material for 3′-demethoxy epipodophyllotoxin derivatives of the present invention.

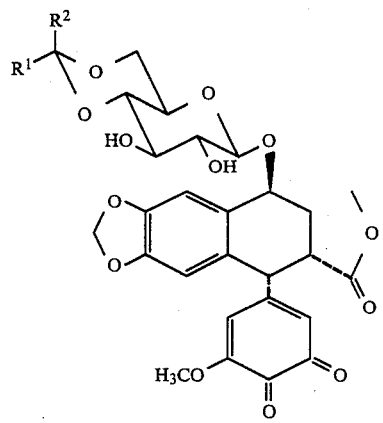

IIIa $R^1$ = $CH_3$; $R^2$ = H

SUMMARY OF THE INVENTION

The present invention provides 3′-demethoxy epipodophyllotoxin glucoside derivatives of Formula IV

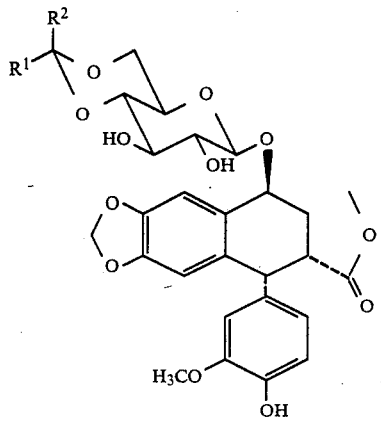

wherein $R^2$ is hydrogen and $R^1$ is selected from the group consisting of $C_1$–$C_{10}$ alkyl, $C_2$–$C_{10}$ alkenyl, $C_3$–$C_7$ cycloalkyl, furyl, thienyl, pyridyl, pyrrolyl, $C_6$–$C_{10}$ aryl and $C_7$–$C_{14}$ aralkyl, said aryl and aralkyl rings optionally bearing one or more substituents selected from halo, $C_1$–$C_4$ alkyl, nitro, hydroxy, $C_1$–$C_4$ alkoxy, $C_1$–$C_4$ alkanoyloxy, cyano, amino, $C_1$–$C_4$ alkylamino, di($C_1$–$C_4$alkyl)amino, carboxy, $C_1$–$C_4$ alkylthio, mercapto, $C_2$–$C_4$ alkenoylamino, $C_2$–$C_4$ alkenyl and carbamoyl; or $R^1$ and $R^2$ are each $C_1$–$C_{10}$ alkyl; or $R^1$ and $R^2$ and the carbon atom to which they are attached join to form a $C_5$–$C_6$ cycloalkyl group. A preferred embodiment provides compounds of Formula IV wherein $R^2$ is H, and $R^1$ is selected from $C_1$–$C_{10}$ alkyl and thienyl, with methyl being the most preferred.

Another aspect provides a method for inhibiting tumors in a mammalian host comprising administering to a tumor-bearing host a tumor-inhibiting amount of a compound of Formula IV.

A further aspect provides a pharmaceutical composition comprising a compound of Formula IV in a pharmaceutically acceptable carrier.

DETAILED DESCRIPTION OF THE INVENTION

Compounds of the present invention may be prepared by the reaction sequence shown in Scheme I wherein $R^3$ is $C_1-C_5$ alkyl or aryl-$C_1-C_5$ alkyl, and the term "EPIPODO" is used to represent the fragment.

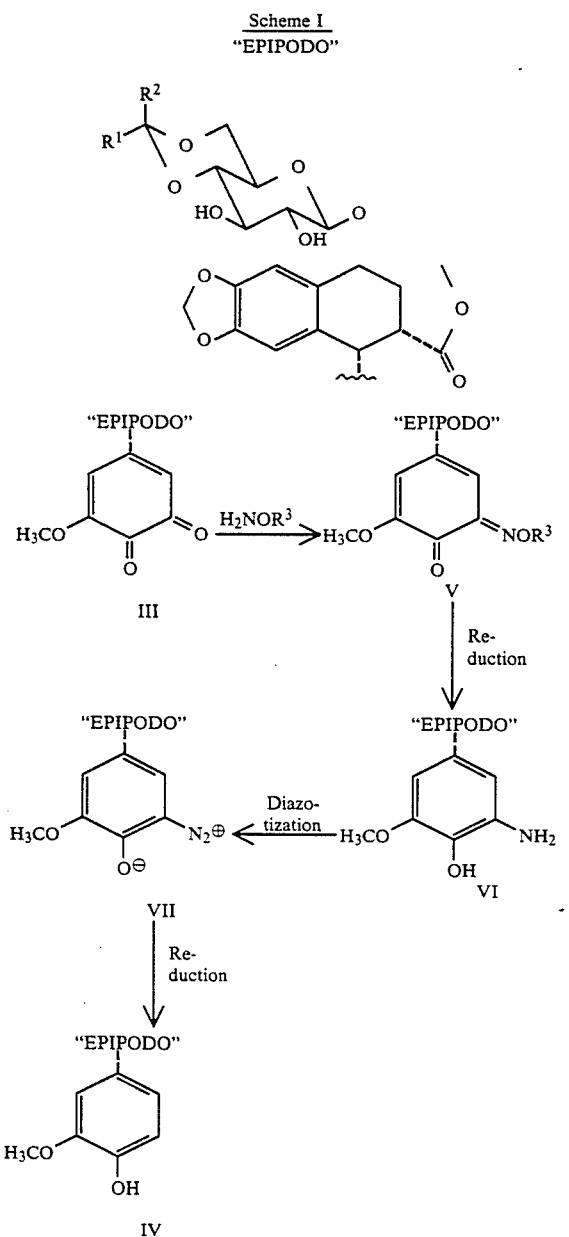

The ortho-quinones III are, as previously mentioned, known compounds that may be prepared by oxidizing 4'-dimethylepipodophyllotoxin glucosides according to the procedure described in US 4,609,644 (J. Nemec, 1986). Reaction of the ortho-quinones III with an O-substituted hydroxylamine, or an acid addition salt thereof, in an inert organic solvent provides the corresponding 3'-oxime ether V. The reaction is preferably carried out at room temperature for a period sufficient to obtain the mono oxime ether, for example from about 30 minutes to about one hour. The products thus formed may be isolated and purified e.g. by flash chromatography; or alternatively, they may be reduced directly, without first being isolated, to the corresponding amine compound of Formula VI. Reduction of the oxime ether to the corresponding 3'-amino compound may be effected by conventional methodologies, e.g. a mild chemical reducing agent, or hydrogenation in the presence of a suitable catalyst such as Pt, Pd, Ni, Ru or Rh. Catalytic hydrogenation is preferably employed. Amine compounds of Formula VI may also be prepared directly from the ortho-quinone III by treatment with ammonia or an alkylamine at room temperature; reaction with the latter yields both the amine VI and the corresponding alkyl substituted amine. The preferred preparative method is the reduction of the oxime ether of Formula V. Diazotization of VI in an inert solvent at reduced temperature followed by aqueous work-up provides the diazonium salt VII. Reduction of the diazonium salt using reagents known in the art for this purpose, such as hypophosphorous acid, sodium borohydride, or an excess of thiophenol provides 3'-demethoxy-4' demethylepipodophyllotoxin of Formula IV.

BIOLOGICAL ACTIVITY

3'-Demethoxy etoposide was evaluated for its antitumor activity against transplantable murine P388 leukemia.

Female $CDF_1$ mice were implanted intraperitoneally with a tumor inoculum of $10^6$ ascites cells of P388 murine leukemia and treated with various doses of a test compound; four mice were used for each dose level and ten were used as saline-treated control. The compounds were administered by intraperitoneal injection on days 5 and 8 (day 1 being the day of tumor implantation). Antitumor activity was expressed as % T/C which is the ratio of the median survial time (MST) of drug-treated group to the MST of saline-treated control group. A compound showing a % T/C value of 125 or greater is generally considred to have significant antitumor activity in the P388 test. The experiment lasted 31 days at the end of which time the number of survivors was noted. Table I presents the results of the above-described evaluation; only the maximum % T/C and the dose showing the maximum effect are reported.

TABLE 1

| Antitumor activity against P388 Leukemia | | |
|---|---|---|
| Compound | Dose (mg/kg/inj.) | Max. % T/C |
| 3'-Demethoxy etoposide | >40 | 245 |
| Etoposide | 60 | 260 |

It is apparent from the animal test results provided above that compounds of formula IV possess effective inhibitory action against mammalian tumors. Accordingly, this invention provides a method for inhibiting mammalian tumors which comprises administering an effective tumor-inhibiting dose of an antitumor compound of formula IV to a tumor bearing host.

Another aspect of this invention provides a pharmaceutical composition which comprises an effective tumor-inhibiting amount of an antitumor compound of formula IV and a pharmaceutically acceptable carrier. These compositions may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preprations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens for a given mammalian host can be readily ascertained by those skilled in the art. It will, of course, be appreciated that the actual dose used will vary according to the particular composition formulated, the particular compound used, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following examples are for illustrative purposes only and should not be construed as limiting the scope of the invention.

In the following examples, all temperatures are given in degrees Centigrade. Melting points were recorded on a Thomas-Hoover capillary melting point apparatus and are uncorrected. $^1$H NMR spectra were recorded either on a Bruker WM 360 or a Varian VX2 200 spectrophotometer (using CDCl$_3$ as an internal reference). Chemical shifts are reported in δ units and coupling constants in Hertz. Splitting patterns are designated as follows: s, singlet; d, doublet; t, triplet; q, quartet; m, multiplet; bp, broad peak; and dd, doublet of doublet. Infrared spectra were determined either on a Beckman Model 4240 or a Perkin-Elmer 1800 Fourier Transform Infrared Spectrophotometer and are reported in a reciprocal centimeters (cm$^{-1}$). Thin-layer chromatography (TLC) was carried out on precoated silica gel plates (60F-254) using UV light and/or iodine vapors as visualizing agents. High and low resolution mass spectra were recorded on KRATOS MS 50 and KRATOS MS 25RFA Spectrophotometer, respectively. "Flash Chromatography" refers to the method described by Still (Still, W.C. et al, J. Org. Chem., 1978, 43:2923) and was carried out using either E. Merck silica gel (200–400 mesh) or Woelm silica gel (32–63 μm). All evaporations of solvents were performed under reduced pressure.

EXAMPLE 1

Etoposide-ortho-quinone-3'-O-methyloxime Va

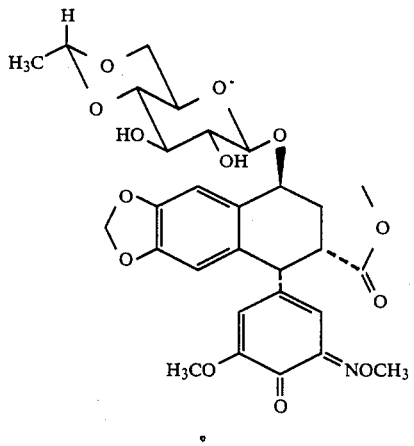

A solution of etoposide ortho-quinone IIIa (350 mg, 0.611 mmol) in a pyridine (20 ml) was treated with a solution of methoxylamine hydrochloride (350 mg, 4.19 mmol) in pyridine (10 ml). The resultant orange solution was stirred for 30 minutes at room temperature and the pyridine was then removed in vacuo. The residue was dissolved in CH$_2$Cl$_2$ (50 ml) and partitioned with H$_2$O (20 ml) and 1N HCl (10 ml). The aqueous layer was further extracted with CH$_2$Cl$_2$ (25 ml) and the combined organic extracts were dried over MgSO$_4$. The solvent was evaporated in vacuo to give a dark orange oil. Flash chromatography on silica gel (14 g) with 5% CH$_3$OH in CH$_2$Cl$_2$ gave 243 mg (66%) of the title compound as an orange solid. Trituration with Et$_2$O provided the analytical sample. On a larger scale, this enzyme is generally not purified but is directly hydrogenated to the amine VIa in an overall yield of ca 70%.

IR (KBr) 3480, 1775, 1670, 1625, 1488, 1237, 1040 cm$^{-1}$.

$^1$H NMR (CDCl$_3$) δ 6.82 (s,1H), 6.56 (s,1H), 6.48 (d,1H), 6.07 (d,1H), 6.01 (d,1H) 5.75 (d,1H), 4,92 (d,1H), 4.76 (q,1H), 4.66 (d,1H), 4.50 (dd,1H), 4.38 (dd,1H), 4.27 (d,1H), 4.22–4.17 (m,1H), 4.15 (s,3H), 3.79 (s,3H), 3.78–3.74 (m,1H), 3.63–3.58 (m,1H), 3.44 (dd,1H), 3.38–3.30 (m,3H), 2.95–2.87 (m,1H), 1.40 (d,3H).

Anal. Calcd for C$_{29}$H$_{31}$NO$_{13}$: C,57.90; H,5.19; N,233. Found: C,56.01; H,5.04; N,2.41.

EXAMPLE 2

3-Amino-3'-demethoxy etoposide VIa

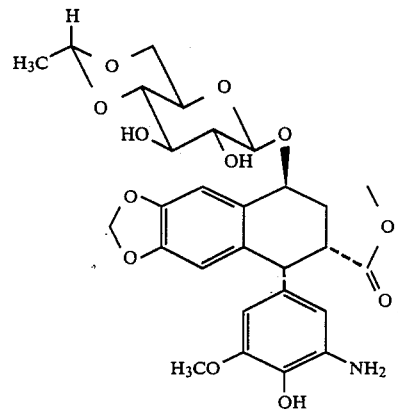

The crude oxime Va obtained from etoposide ortho-quinone IIIa (4.1 g, 7.2 mmol) and methoxylamine hydrochloride (4.1 g, 49 mmol) by the procedure described in Example 1 was dissolved in reagent alcohol (275 ml) and treated with 20% palladium hydroxide on carbon (290 mg) and 10% palladium on carbon (1.6 g). The mixture was hydrogenated at 40-50 psi H$_2$. After 16 h, the mixture was filtered through Celite, washed with ethyl acetate, and the solvent was evaporated. The crude product was purified by flash chromatography on 300 g. E. Merck 230–400 mesh silica gel using 8:2 EtOAc/hexane as eluent to provide 2.89 g (70% overall) of the title compound as a white solid. Recrystallization from ethanol gave the analytical sample.

IR (KBr) 3455, 1775, 1615, 1490, 1235, 1070, 1030, 1000, 930 cm$^{-1}$.

$^1$H NMR (CDCl$_3$) δ 6.76 (s,1H0, 6.48 (s,1H), 6.37 (d,1H), 5.96 (ABq,2H), 5.65 (d,1H), 4.87 (d,1H), 4.73 (q,1H), 4.61 (d,1H), 4.47 (d,1H), 4.38 (dd,1H), 4.23–4.16

(m,2H), 3.78 (s,3H), 3.76-3.72 (m,1H), 3.60-3.55 (m,1H), 3.42 (dd,1H), 3.37-3.30 (m,2H), 3.21 (dd,1H), 2.97-2.88 (m,1H), 1.37 (d,3H).

Anal. Calcd for $C_{28}H_{31}NO_{12}$: C,58.63; H,5.45; N,2.44. Found: C,57.85; H,5.76; N,2.35

EXAMPLE 3

Etoposide 3' 0diazonium hydroxide inner salt VIIa

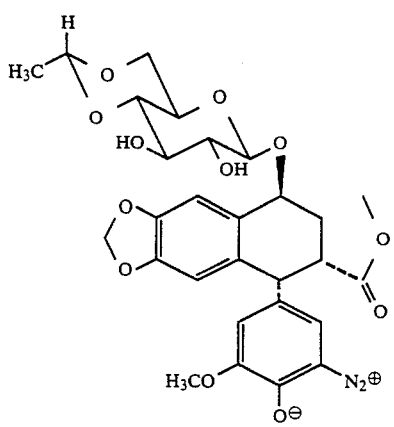

Glacial acetic acid (3.0 ml, 26.2 mmol) followed by $NaNO_2$ (0.15 g, 2.17 mmol) were added to a solution of 3'-aminoetoposide (product of Example 2, 0.22 g, 0.384 mmol) in dry THF (17 ml) stirring at 0° C. under $N_2$. The reaction mixture was stirred for 3.4 hours at 0° C. and poured into 150 ml of $CH_2Cl_2$. The dark red organic layer was washed with 100 ml of aqueous $NaHCO_3$. The combined organic extracts were washed with 100 ml of saturated $NaHCO_3$, dried over $MgSO_4$ and concentrated in vacuo to provide 0.177 g (79%) of a reddish orange solid: mp. slow decomposition 150° C.

IR (KBr) 3440 (b), 2930, 2160, 2120, 1779 cm$^{-1}$.

$^1$H NMR (CDCl$_3$) δ 6.78 (s,1H), 6.73 (s,1H), 6.52 (s,1H), 5.97 (d,J=8.3Hz,2H), 5.82 (s,1H), 4.86 (d,J=2.2Hz, 1H), 4.72 (m,1H), 4.54 (d,J=7.6Hz,1H), 4.43 (t,J=9.0Hz,1H0, 4.35 (d,J=5.1Hz,1H), 4.26 (t,J=8.3Hz,1H), 4.14 (m,1H), 3.71 (s,3H), 3.55 (t,J=9.7Hz,1H), 3.40 (t,J=8.1Hz, 1H), 3.3 (bm,4H), 3.02 (m,1H), 1.35 (d,J=4.9Hz,3H).

EXAMPLE 4

3'-Demethoxy etoposide IV.

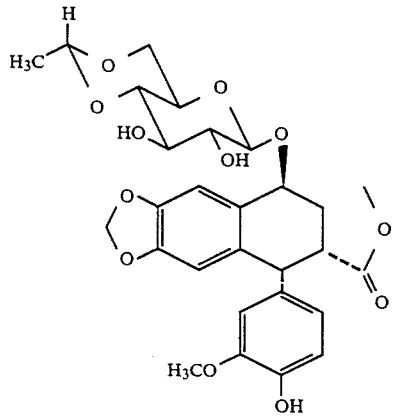

The crude etoposide diazonium salt of Example 3 (1.03 g, 1.76 mmol) was dissolved in absolute methanol (100 ml) and treated with sodium borohydride powder (400 mg) followed after 5 minutes by the addition of glacial acetic acid (5 ml). The mixture was stirred at room temperature for 2 hours, the solvent was evaporated in vacuo, and the residue was treated with $H_2O$ (100 ml) and extracted with $CH_2Cl_2$ (100 ml then 2×50 ml). The combined extracts were washed with saturated aqueous sodium bicarbonate (25 ml) and brine (75 ml) and dried over $MgSO_4$. Rotary evaporation followed by flash chromatography on silica gel (32 g) using 3-4% $CH_3OH$ in $CH_2CH_2$ as eluant provided 400 mg (41%) of the title compound as a colorless solid, mp 190°-195° C.

IR (KBr) 3455, 1775, 1515, 1485, 1388, 1170, 1090, 1075, 1035, 1005, 933, 700 cm$^{-1}$.

$^1$H NMR (CDCl$_3$) δ 6.99 (d, 1H,J=1.7Hz), 6.79 (s, 1H), 6.65 (d,1H,J=8.2Hz), 6.51 (s, 1H), 6.01 (dd,1H,J=1.7 and 8.2Hz), 5.96 (d,2H), 5.50 (s, 1H), 4.87 (d,1H,J=3.4Hz), 4.73 (q,1H,J=5Hz), 4.64 (d,1H,J=7.6Hz), 4.57 (d,1H,J=5.2Hz), 4.39 (dd,1H), 4.21-4.13 (m,2H), 3.85 (s,3H), 3.71 (dd,1H), 3.56 (dd,1H), 3.43 (m,1H), 3.33-3.30 (m,2H), 3.23 (dd,1H,J=5.2 and 14.1Hz), 2.91-2.82 (m,1H), 2.66 (br s, 1H), 2.39 (br s, 1H), 1.37 (d,3H,J=5Hz). Anal. calcd for $C_{28}H_{30}O_{12}$: C, 60.21; H, 5.41. Found: C, 59.45; H, 5.57.

EXAMPLE 5

The procedures described in Examples 1 to 4 are repeated with the exception that etoposide ortho-quinone is replaced with epipodophyllotoxin glucoside ortho-quinones having $R^1$ and $R^2$ as shown below to provide the corresponding 3'-demethoxy derivatives.

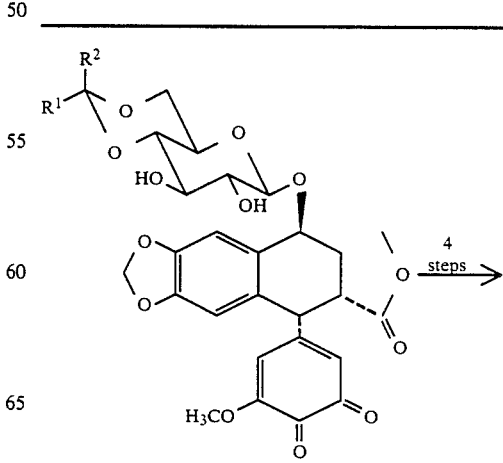

-continued

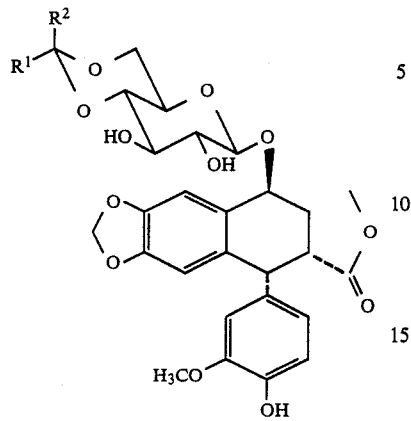

| $R^1$ | $R^2$ |
|---|---|
| 2-thienyl | H |
| 2-furyl | H |
| cyclohexyl | H |
| phenyl | H |
| benzyl | H |
| 4-methylphenyl | H |
| 3-methoxyphenyl | H |
| 4-hydroxyphenyl | H |
| 4-(N,N—dimethylphenyl) | H |
| 2-chlorophenyl | H |
| methyl | methyl |
| ethyl | methyl |
| $R^1 + R^2 = (CH_2)_4$ | |
| $= (CH_2)_5$ | |

What is claimed is:

1. A compound having the formula

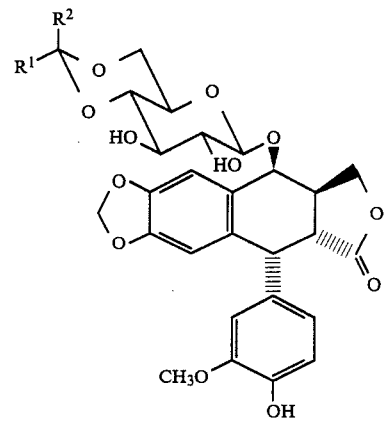

wherein $R^2$ is hydrogen and $R^1$ is selected from the group consisting of $C_1$–$C_{10}$ alkyl, $C_2$–$C_{10}$ alkenyl, $C_3$–$C_7$ cycloalkyl, furyl, thienyl, $C_6$–$C_{10}$ aryl, and $C_7$–$C_{14}$ aralkyl, said aryl and aralkyl rings being unsubstituted or substituted with one or more substituents selected from the group consisting of halo, $C_1$–$C_4$ alkyl, nitro, hydroxy, $C_1$–$C_4$ alkoxy; or $R^1$ and $R^2$ are each $C_1$–$C_{10}$ alkyl; or $R^1$ and $R^2$ and the carbon atom to which they are attached join to form a $C_5$–$C_6$ cycloalkyl group.

2. A compound of claim 1 wherein $R^2$ is H and $R^1$ is methyl or 2-thienyl.

3. A compound of claim 2 wherein $R^1$ is methyl.

4. A pharmaceutical composition which comprises a compound of claim 1 and a pharmaceutically acceptable carrier.

* * * * *

UNITED STATES PATENT AND TRADEMARK OFFICE
CERTIFICATE OF CORRECTION

PATENT NO. : 4,888,419

DATED : December 19, 1989

INVENTOR(S) : Mark G. Saulnier, et al.

It is certified that error appears in the above-identified patent and that said Letters Patent is hereby corrected as shown below:

Column 1, Formulas I and II; Column 2, Formulas III and IV; Column 5, Formula Va; Column 6, Formula IVa; Column 7, Formulas VIIa and IV; Column 8, the formula at the bottom of the column; and the formula at Column 9, in each of the formulas referred to, the portion of the formula reading

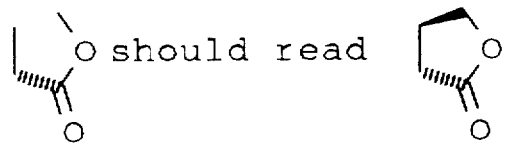

UNITED STATES PATENT AND TRADEMARK OFFICE
CERTIFICATE OF CORRECTION

PATENT NO. : 4,888,419

DATED : December 19, 1989

INVENTOR(S) : Mark G. Saulnier, et al.

It is certified that error appears in the above-identified patent and that said Letters Patent is hereby corrected as shown below:

In Column 3, the formula under the heading "EPIPODO", the portion of the formula reading

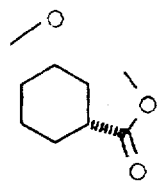 should read 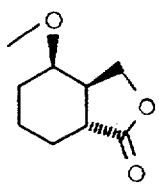

Signed and Sealed this

Sixth Day of August, 1991

Attest:

HARRY F. MANBECK, JR.

Attesting Officer

Commissioner of Patents and Trademarks